(12) United States Patent
Tabuchi et al.

(10) Patent No.: US 9,012,503 B2
(45) Date of Patent: Apr. 21, 2015

(54) OPHTHALMIC COMPOSITION

(75) Inventors: Nobuhito Tabuchi, Tokyo (JP); Chieko Inoue, Tokyo (JP); Manabu Hattori, Tokyo (JP); Miyuki Miyake, Tokyo (JP); Hazuki Tsutsui, Tokyo (JP)

(73) Assignee: Lion Corporation, Tokyo (JP)

( * ) Notice: Subject to any disclaimer, the term of this patent is extended or adjusted under 35 U.S.C. 154(b) by 134 days.

(21) Appl. No.: 13/377,867

(22) PCT Filed: Jun. 25, 2009

(86) PCT No.: PCT/JP2009/061591
§ 371 (c)(1),
(2), (4) Date: Dec. 13, 2011

(87) PCT Pub. No.: WO2010/150378
PCT Pub. Date: Dec. 29, 2010

(65) Prior Publication Data
US 2012/0095097 A1    Apr. 19, 2012

(51) Int. Cl.
*A61K 31/203* (2006.01)
*A61K 31/22* (2006.01)
*A61K 31/23* (2006.01)
*A61K 9/00* (2006.01)
A61K 9/08 (2006.01)
A61K 47/10 (2006.01)

(52) U.S. Cl.
CPC ............ *A61K 31/203* (2013.01); *A61K 9/0048* (2013.01); *A61K 31/22* (2013.01); *A61K 31/23* (2013.01); *A61K 9/08* (2013.01); *A61K 47/10* (2013.01)

(58) Field of Classification Search
None
See application file for complete search history.

(56) References Cited

FOREIGN PATENT DOCUMENTS

| | | |
|---|---|---|
| CN | 101028240 A | 9/2007 |
| JP | 5-331056 A | 12/1993 |
| JP | 6-40907 A | 2/1994 |
| JP | 6-247853 A | 9/1994 |
| JP | 2002-332225 A | 11/2002 |
| JP | 2003-113078 A | 4/2003 |
| JP | 2007-169232 A | 7/2007 |
| JP | 2008-94839 A | 4/2008 |

OTHER PUBLICATIONS

Edited by Japan Pharmaceutical Excipients Council, Iyakuhin Tenkabutsu Jiten 2007, Yakuji Nippon Ltd., 2007, pp. 266 to 269.
International Search Report issued in PCT/JP2009/061591, dated Jul. 28, 2009.

*Primary Examiner* — Zohreh Fay
(74) *Attorney, Agent, or Firm* — Birch, Stewart, Kolasch & Birch, LLP

(57) ABSTRACT

Disclosed is an ophthalmic composition containing (A) not less than 50,000 units/100 mL of vitamin A, (B) not less than 0.4 W/V % of a polyoxyethylene polyoxypropylene glycol, and (C) trometamol.

14 Claims, No Drawings

OPHTHALMIC COMPOSITION

TECHNICAL FIELD

This invention relates to an ophthalmic composition containing vitamin A at a high concentration.

BACKGROUND ART

Attention has been drawn to vitamin A as being an effective ingredient for preventing or treating keratoses such as of the cornea and conjunctiva and also of the skin mucosa. On the other hand, vitamin A that is a lipophilic vitamin is very sensitive to air, light, heat, acids, metal ions and the like and is particularly very unstable in aqueous solutions, with a difficulty involved in stably formulating it in ophthalmic compositions such as eye drops and the like.

For techniques of stabilizing such unstable vitamin A, there have been hitherto proposed a method of stabilization with nonionic surfactants such as polyethylene hardened castor oil and the like (see, for example, JP-A H05-331056: Patent Document 1), a method of stabilization with vitamin Es that are a hydrophobic antioxidant (see, for example, JP-A H06-247853: Patent Document 2), and a technique of stabilization from the aspect of a container or package (see, for example, JP-A H06-40907: Patent Document 3, and JP-A 2003-113078: Patent Document 4), and a stabilization technique wherein preparation is carried out by high-energy emulsification (see, for example, JP-A 2002-332225: Patent Document 5). However, the prior-art techniques have not been well satisfactory with respect to the level of stability necessary for medical products in high concentration systems (of not lower than 50,000 units). In view of the above, there has been demanded a technology of further increasing the stabilization of vitamin A in ophthalmic compositions formulated with a high concentration of vitamin A.

PRIOR ART DOCUMENTS

Patent Documents

Patent Document 1: JP-A H05-331056
Patent Document 2: JP-A H06-247853
Patent Document 3: JP-A H06-40907
Patent Document 4: JP-A 2003-113078
Patent Document 5: JP-A 2002-332225

SUMMARY OF THE INVENTION

Problems to be Solved by the Invention

The invention has been made under such circumstances as set out above and has for its object the provision of an ophthalmic composition formulated with a high concentration of stabilized vitamin A and also of a stabilizing method of vitamin A.

Means for Solving the Problems

We made intensive studies in order to achieve the above object and, as a result, found that when at least 0.4 W/V % of polyoxyethylene polyoxypropylene glycol and trometamol are formulated in an ophthalmic composition containing at least 50,000 units/100 mL of vitamin A, the stability of vitamin A can be significantly enhanced, thereby arriving at completion of the invention.

Accordingly, the invention provides the following ophthalmic composition and stabilizing method of vitamin A.

[1] An ophthalmic composition including (A) at least 50,000 units/100 mL of vitamin A, (B) at least 0.4 W/V % of polyoxyethylene polyoxypropylene glycol and (C) trometamol.

[2] The ophthalmic composition as recited in [1], wherein a content of the ingredient (A) is at least 100,000 units/100 mL.

[3] The ophthalmic composition as recited in [1], wherein a content of the ingredient (A) is at least 200,000 units/100 mL.

[4] The ophthalmic composition as recited in [1], wherein a content of the ingredient (A) is at least 300,000 units/100 mL.

[5] The ophthalmic composition as recited in any one of [1] to [4], further including (D) an antioxidant.

[6] The ophthalmic composition as recited in [5], wherein the ingredient (D) is vitamin E and/or dibutylhydroxytoluene.

[7] The ophthalmic composition as recited in any one of [1] to [6], wherein the ingredient (A) is retinol palmitate, retinol acetate or retinoic acid.

[8] The ophthalmic composition as recited in any one of [1] to [7], wherein a ratio by weight between the ingredient (B) and the ingredient (C) expressed as (B):(C) is at 1:30 to 30:1.

[9] A method for stabilizing vitamin A comprising:
formulating at least 0.4 W/V % of polyoxyethylene polyoxypropylene glycol and (C) trometamol in an ophthalmic composition containing at least 50,000 units/100 mL of vitamin A.

Advantageous Effect of the Invention

According to the invention, there can be provided a vitamin A-containing ophthalmic composition wherein vitamin A is stabilized even when the vitamin A is formulated at high concentration and also a method for stabilizing vitamin A.

EMBODIMENT FOR CARRYING OUT THE INVENTION

The invention is now described in detail. The ophthalmic composition of the invention includes (A) at least 50,000 units/100 mL of vitamin A, (B) at least 0.4 W/V % of polyoxyethylene polyoxypropylene glycol and (C) trometamol. It will be noted that another purpose of the invention is to provide an ophthalmic composition having a dry eye-improving effect, and a further effect of the invention is a dry eye-improving effect.

(A) Vitamin A

As vitamin A, there may be mentioned, aside from vitamin A itself, vitamin A-containing mixtures such as vitamin A oil, vitamin A derivatives such as vitamin A fatty acid esters, and the like. More particularly, vitamin A includes retinol palmitate, retinol acetate, retinol, retinoic acid, retinoide and the like. Of these, retinol palmitate, retinol acetate, and retinoic acid are preferred. Retinol palmitate is commercially sold usually as having one million to 1.8 million international units (hereinafter abbreviated as units or I.U.), for which specific mention is "Retinol palmitate" (1.7 million I.U./g), made by Roche Vitamin Japan Co., Ltd.).

The ingredients (A) may be used singly or in appropriate combination of two or more. The content is at least 50,000 units/100 mL relative to the total amount of the ophthalmic composition. Vitamin A has a corneal and conjunctival disorder treating effect and an improving effect of dry eyes, tired eyes and bleary eyes, and such effects can be more pronouncedly shown when its content of at least 50,000 units/ 100 mL is used. From the standpoint of these effects, the amount of the ingredient (A) is preferably at least 100,000 units/100 mL, more preferably at least 200,000 units/100 mL and much more preferably at least 300,000 units/100 mL. The upper limit is preferably not greater than 500,000 units/100 mL from the viewpoint of stability. When expressed in terms of W(weight)/V(volume)%(g/100 mL), the above amount is preferably at 0.03 to 0.3 W/V % although depending on the units of vitamin A being formulated.

(B) Polyoxyethylene polyoxypropylene glycol

In the invention, when using (B) polyoxyethylene polyoxypropylene glycol, even an ophthalmic composition containing at least 50,000 units/100 mL is able to keep stability thereof, does not have eye irritation and improve the effects of treating a cornea damage and dry eyes. These effects are unsatisfactory when using surfactants, such as sorbitan fatty acid esters, polyoxyethylene hardened castor oil and the like, which have been well used, for example, in eye drops. Polyoxyethylene polyoxypropylene glycol is not critical in type and those described in Japanese Pharmaceutical Excipients (JPE) may be used. The preferred average degree of polymerization of ethylene oxide is 4 to 200, more preferably 20 to 200 and the average degree of polymerization of propylene oxide is preferably 5 to 100, more preferably 20 to 70, and either a block copolymer or a random polymer may be used.

In particular, mention is made of polyoxyethylene (200) polyoxypropylene (70) glycol: Lutrol F127 (made by BASF), Uniloob 70DP-950B (made by NFO Corporation), polyoxyethylene (120) polyoxypropylene (40) glycol (Pluronic F-87), polyoxyethylene (160) polyoxypropylene (30) glycol (Pluronic F-68, otherwise known as Poloxamer 188): Pronon #188P (made by NFO corporation) and the like, polyoxyethylene (42) polyoxypropylene (67) glycol (Pluronic P123, otherwise known as Poloxamer 403), polyoxyethylene (54) polyoxypropylene (39) glycol (Pluronic P85):Pronon #235P (made by NFO Corporation) and the like, polyoxyethylene (20) polyoxypropylene (20) glycol (Pluronic L-44), Tetronic and the like. Of these, polyoxyethylene (200) polyoxypropylene (70) glycol, polyoxyethylene (160) polyoxypropylene (30) glycol, and polyoxyethylene (54) polyoxypropylene (39) glycol are preferred.

The ingredients (B) may be used singly or in appropriate combination of two or more. The content is at least 0.4 W/V %, preferably 0.4 to 5 W/V %, more preferably 0.5 to 3 W/V %, much more preferably 0.6 to 2 W/V %, and most preferably 1 to 2 W/V %, relative to the total amount of the ophthalmic composition. If the amount is less than 0.4 W/V %, a difficulty is involved in solubilizing vitamin A and in view of storage stability of vitamin A, the amount is preferably not greater than 5 W/V %.

From the standpoint of the storage stabilization of vitamin A, the ratio between ingredient (A) and ingredient (B), expressed as [(A) vitamin A units/100 mL]/[(B) polyoxyethylene polyoxypropylene glycol g/100 mL], is preferably at 10,000 to 150,000, more preferably at 15,000 to 100,000 and much more preferably at 25,000 to 50,000.

(C) Trometamol

From the standpoint of improving the storage stability of vitamin A, it is preferred to formula trometamol in the ophthalmic composition of the invention. For the first time, we have found that trometamol has an effect of improving the storage stability of vitamin A. This mechanism is not clearly known and may be considered, for example, in the following way. Polyoxyethylene polyoxypropylene glycol is a nonionic surfactant that has a polyoxyethylene (EO) chain and a polyoxypropylene (PO) chain. Vitamin A is wrapped with the EO chain kept outside and also with the PO chain kept inside, thereby forming a micelle. The coexistence of trometamol permits the —$NH_2$ group present in trometamol to be directly bound to the ether bond of the EO chain, resulting in the strong structure of the micelle. Moreover, trometamol binds to the EO chain located at the outside of the micelle so that the micelle structure is rendered strong with the degree of freedom being lowered, eventually leading to the lowering of molecular mobility of the PO chain inside the micelle. In view of the above, it is considered that trometamol contributes to the stabilization of the micelle formed from vitamin A and polyoxyethylene polyoxypropylene glycol and, as a consequence, contributes to the storage stability of vitamin A.

The content of trometamol (C) is preferably at 0.01 to 5 W/V %, more preferably at 0.05 to 5 W/V %, much more preferably at 0.1 to 3 W/V % and most preferably at 0.5 to 2 W/V %, relative to the total amount of the ophthalmic composition. If the content is less than 0.01 W/V %, there is concern that the effect on the storage stabilization of vitamin A becomes unsatisfactory. Over 5 W/V %, there is concern that eye irritation occurs. From the standpoint of the storage stabilization of vitamin A, the ratio by weight between the ingredient (B) and the ingredient (C) expressed by (B):(C) is preferably at 1:30 to 30:1, more preferably at 1:20 to 20:1, much more preferably at 1:10 to 10:1 and most preferably at 1:10 to 3:1.

(D) Antioxidant

The ophthalmic composition of the invention is preferably formulated with an antioxidant from the standpoint of improving the storage stability of vitamin A. As an antioxidant, mention is made of vitamin Es such as
d-α-tocopherol, d-β-tocopherol, d-γ-tocopherol,
d-δ-tocopherol, dl-α-tocopherol, d-α-tocopherol acetate,
dl-α-tocopherol acetate, dl-δ-tocopherol acetate,
dl-γ-tocopherol acetate, dl-δ-tocopherol acetate,
dl-α-tocopherol nicotinate and the like,
lipophilic antioxidants such as dibutylhydroxytoluene, butylhydroxyanisole and the like, vitamin C, water-soluble antioxidants such as hydroquinone, cysteine, glutathione and the like, etc. Of these, lipophilic antioxidants such as vitamin E and the like are preferred, among which d-α-tocopherol acetate and dibutylhydroxytoluene are more preferred and d-α-tocopherol is much more preferable. It is also preferred to use vitamin E and dibutylhydroxytoluene in combination.

The antioxidants may be used singly or in combination of two or more. The content is preferably at 0.005 to 5 W/V % relative to the total amount of the ophthalmic composition, within which the storage stability of vitamin A can be improved, and is more preferably at 0.005 to 1 W/V % and much more preferably at 0.005 to 0.2 W/V %.

The ophthalmic composition of the invention may be formulated, aside from the above ingredients, with a variety of ingredients being formulated in ophthalmic compositions without detracting the effect of the invention. These ingredients include polyhydric alcohols, surfactants other than the ingredient (B), buffering agents, thickening agents, sugars, pH adjusters, antiseptics, tonicity agents, stabilizing agents, algefacients, drugs, water and the like. These may be used singly or in appropriate combination of two or more and can be formulated in appropriate amounts.

Polyhydric alcohols include glycerine, propylene glycol, butylene glycol, polyethylene glycol and the like. The content of the polyhydric alcohol is preferably at 0.01 to 5 W/V %, more preferably at 0.05 to 3 W/V %, relative to the total amount of the ophthalmic composition.

Surfactants other than the ingredient (B) may be used in combination, for which mention is made of polyoxyethylene hardened castor oil, a polyoxyethylene sorbitan fatty acid ester (Polysorbate 80) and the like. The parallel usage permits stability to be improved. The content of the surfactant is preferably at 0.0001 to 5 W/V %, more preferably at 0.005 to 3 W/V %, relative to the total amount of the ophthalmic composition. It will be noted that from the standpoints of the effect of treating corneal and conjunctival damages and the healing effect of dry eyes, it is favorable to use these surfactants in reduced amounts and their content is preferably at not greater than 0.5 W/V %.

Examples of the buffering agent include boric acid or borates (borax and the like), citric acid or citrates (sodium citrate and the like), phosphoric acid or phosphates (sodium hydrogen phosphate and the like), tartaric acid or tartarates (sodium tartarate and the like), gluconic acid or gluconates (sodium gluconate and the like), and acetic acid or acetates (sodium acetate and the like), of which boric acid and borax are preferred when they are used in combination because a high antiseptic effect is obtained therefrom. The content of the buffering agent is preferably at 0.001 to 10 W/V %, more preferably at 0.01 to 5 W/V %, relative to the total amount of the ophthalmic composition. The formulation of boric acid or citric acid allows vitamin A to be more stabilized.

The thickening agents include, for example, polyvinylpyrrolidone, hydroxyethyl cellulose, hydroxypropyl methyl cellulose, methyl cellulose, polyvinyl alcohol, sodium hyaluronate, sodium chondroitin sulfate, polyacrylic acid, carboxyvinyl polymer and the like. The formulation of these ingredients permits retentivity to be enhanced and the corneal and conjunctival disorder treating effect to be more improved. The content of the thickening agent is, for example, at 0.001 to 10 W/V %, preferably at 0.001 to 5 W/V % and more preferably at 0.01 to 3 W/V %.

Sugars include glucose, cyclodextrin, xylitol, sorbitol, mannitol and the like. It will be noted that these may be in any form of a D isomer, L isomer or DL isomer. The content of the sugar relative to the total amount of the ophthalmic composition is, for example, at 0.001 to 10 W/V %, preferably at 0.005 to 5 W/V % and more preferably at 0.01 to 3 W/V %.

As a pH adjuster, it is preferred to use an inorganic acid or inorganic alkaline agents. Examples of the inorganic acid include (diluted) hydrochloric acid. Examples of the inorganic alkaline agent include sodium hydroxide, potassium hydroxide, sodium carbonate, sodium hydrogen carbonate, and the like. Of these, hydrochloric acid and sodium hydroxide are preferred. The pH (20° C.) of the ophthalmic composition of the invention is preferably at 4.0 to 9.0, more preferably at 5.0 to 8.0 and much more preferably at 6.0 to 8.0. It will be noted that in the practice of the invention, the pH is measured by use of a pH osmometer (HOSM-1, made by DKK-Toa Corporation) at 20° C. The content of the pH adjuster relative to the total amount of the ophthalmic composition is, for example, at 0.00001 to 10 W/V %, preferably at 0.0001 to 5 W/V % and much more preferably at 0.001 to 3 W/V %.

As an antiseptic, mention is made, for example, of benzalkonium chloride, benzethonium chloride, sorbic acid or its salts, para-oxybenzoic acid esters (methylparaben, ethylparaben, propylparaben and the like), chlorhexidine gluconate, thimerosal, phenylethyl alcohol, alkyldiaminoethyl glycine hydrochloride, polyhexanide hydrochloride, polidronium chloride and the like. The content of the antiseptic relative to the total amount of the ophthalmic composition is, for example, at 0.00001 to 5 W/V %, preferably at 0.0001 to 3 W/V % and more preferably at 0.001 to 2 W/V %.

It will be noted that in the practice of the invention, the content of a cationic surfactant selected from benzalkonium chloride and benzetonium chloride (part of which is a cationic antiseptic) and a hydrophobic antiseptic selected from a para-oxybenzoic acid ester (methylparaben, ethylparaben, propylparaben or the like) and chlorobutanol is preferably, from the standpoints of the corneal and conjunctival disorder treating effect and the dry eye improving effect, at not greater than 0.004 W/V %, more preferably at not greater than 0.003 W/V %, provided that it is much more preferred that these are not formulated without incorporation thereof. The mechanism of impeding the corneal and conjunctival disorder treating effect is not known, but is considered as follows. Polyoxyethylene polyoxypropylene glycol (B) wraps around vitamin A while keeping the EO chain outside and the PO chain inside thereby forming a micelle. This micelle adsorbs on the cornea surface to permit vitamin A to be absorbed in the cornea. Because the condition of the micelle surface is changed owing to the surface activity of the cationic surfactant and also to the high hydrophobicity of the hydrophobic antiseptic, thereby inhibiting the adsorption of the vitamin A on the cornea. Eventually, the corneal and conjunctival disorder treating effect and a dry eye improvement are impeded. On the other hand, those having high hydrophilicity such as sorbic acid or its salt do not influence the condition of the micelle surface, so that the absorption-expediting effect on vitamin A is not inhibited. The above ingredient is a sort of antiseptic, and if no antiseptic is formulated, antiseptic power is ensured by formulating one or more, preferably two or more, of sodium edetate, boric acid and trometamol. In addition, if there is used a unit dose container or a filter-attached container, no formulation of an antiseptic is possible.

The tonicity agent includes, for example, sodium chloride, potassium chloride and the like. The content of the tonicity agent relative to the total amount of the ophthalmic composition is, for example, at 0.001 to 5 W/V %, preferably at 0.01 to 3 W/V % and more preferably at 0.1 to 2 W/V %.

The stabilizing agent includes, for example, sodium edetate, cyclodextrin, a sulfite, dibutylhydroxytoluene and the like. It is to be noted that in the practice of the invention, when a stabilizing agent is formulated, the stability of vitamin A is more improved. The content of the stabilizing agent relative to the total amount of the ophthalmic composition is, for example, at 0.001 to 5 W/V %, preferably at 0.01 to 3 W/V % and more preferably at 0.1 to 2 W/V %.

The algefacient includes, for example, menthol, camphor, borneol, geraniol, linalool, cineol and the like. The content of the algefacient relative to the total amount of the ophthalmic composition is preferably at 0.0001 to 5 W/V %, more preferably at 0.001 to 2 W/V %, much more preferably at 0.005 to 1 W/V % and most preferably at 0.007 to 0.8 W/V %.

As a drug (pharmaceutically effective ingredient), there may be appropriately formulated, for example, a decongestant (e.g. naphazoline hydrochloride, tetrahydrozoline hydrochloride, phenylephrine hydrochloride, epinephrine, ephedrine hydrochloride, dl-methylephedrine hydrochloride, tetrahydrozoline nitrate, naphazoline nitrate or the like), an antiphlogistic/astringent agent (e.g. neostigmine methylsulfate, $\epsilon$-aminocaproic acid, allantoin, berberine chloride, zinc sulfate, zinc lactate, lysozyme chloride, dipotassium glycyrrhizinate, ammonium glycyrrhizinate, glycyrrhetinic acid, methyl salicylate, tranexamic acid, azulene sodium sulfonate or the like), an antihistamine agent (e.g. iproheptine hydrochloride, diphenhydramine hydrochloride, diphenhydramine, isothipendyl hydrochloride, chlorpheniramine maleate or the like), a water-soluble vitamin (activated vitamin $B_2$, vitamin $B_6$, vitamin $B_{12}$ or the like), an amino acid (e.g. potassium L-aspartate, magnesium L-aspartate, aminoethylsulfonic acid, sodium chondroitin sulfate or the like), a sulfa drug or bactericide (e.g. sulfur, isopropylmethylphenol, hinokitiol or the like), an anti-allergenic agent (e.g. cromoglycic acid, ketotifen fumarate, tranilast or the like), a regional anesthetic (e.g. lidocaine, lidocaine hydrochloride, procaine hydrochloride, dibucaine hydrochloride or the like), a mydriatic drug (e.g. cyclopentolate hydrochloride, tropicamide or the like), and a cataract drug (pirenoxine, glutathione or the like).

The content of these ingredients may be appropriately selected depending on the types of preparations and the types of drugs, and the content of the respective ingredients is known in this field of technology. For instance, the content can be appropriately chosen from a range of 0.0001 to 30 W/V %, preferably from 0.001 to 10 W/V %, relative to the total amount of the ophthalmic composition. More particularly, the contents of the respective ingredients relative to the total amount of the ophthalmic composition are just as follows.

With a decongestant, the content is, for example, at 0.0001 to 0.5 W/V %, preferably at 0.0005 to 0.3 W/V % and more preferably at 0.001 to 0.1 W/V %.

With an antiphlogistic/astringent agent, the content is, for example, at 0.0001 to 10 W/V %, preferably at 0.0001 to 5 W/V %.

With an antihistamine agent, its content is, for example, at 0.0001 to 10 W/V %, preferably at 0.001 to 5 W/V %.

With a water-soluble vitamin, its content is, for example, at 0.0001 to 1 W/V %, preferably at 0.0001 to 0.5 W/V %.

With an amino acid, the content is, for example, at 0.0001 to 10 W/V %, preferably at 0.001 to 3 W/V %.

With a sulfur drug or bactericide, the content is, for example, at 0.00001 to 10 W/V %, preferably at 0.0001 to 10 W/V %.

With an anti-allergenic agent, the content is, for example, at 0.0001 to 10 W/V %, preferably at 0.001 to 5 W/V %.

With a regional anesthetic, a mydriatic drug or a cataract drug, the content is, for example, at 0.001 to 1 W/V %, preferably at 0.005 to 1 W/V %.

The ophthalmic composition of the invention may be used as it is in liquid form, or may be prepared as a suspension, a gelling agent or the like. The type of usage particularly includes eye drops (e.g. an ordinary eye drop, an eye drop for contact lenses and the like), eye washes (e.g. an ordinary eye wash, an eye wash used after removal of contact lenses and the like), solutions used upon wearing of contact lenses, solutions used when removing contact lenses and the like.

Where the ophthalmic composition of the invention is in liquid form and is used as an eye drop, its viscosity is preferably at 1 to 100 mPa-second, more preferably at 1 to 50 mPa-second and much more preferably at 1 to 30 mPa-second. It will be noted that the viscosity is measured by use of an E-type viscometer (VISCONIC ELD-R, made by Tokyo Keiki Inc.) at 20° C.

The ophthalmic composition of the invention is not critical with respect to its preparation method. For instance, the composition can be obtained by solubilizing vitamin A in sterilized purified water with the aid of polyoxyethylene polyoxypropylene glycol, followed by adding trometamol and other formulation ingredients and adjusting a pH thereof. Thereafter, the composition can be aseptically filled, for example, in a polyethylene terephthalate container.

According to the invention if vitamin A is formulated in amounts of at least 50,000 units/100 mL, the formulation of polyoxyethylene polyoxypropylene glycol and trometamol enables the vitamin A to be stabilized.

The method for stabilizing vitamin A according to the invention is one wherein at least 0.4 W/V % of polyoxyethylene polyoxypropylene glycol and trometamol (C) are formulated in an ophthalmic composition containing at least 50,000 units/100 mL of vitamin A, and favorable additive ingredients and contents thereof are similar to those of the above-stated ophthalmic composition. The invention is directed to a formulation for an ophthalmic composition containing at least 50,000 units/100 mL and can provide a stabilizer for such vitamin A made up of polyoxyethylene polyoxypropylene glycol and trometamol. In this case, polyoxyethylene polyoxypropylene glycol is formulated in an amount of at least 0.4 W/V % in an ophthalmic composition containing at least 50,000 units/100 mL.

Since vitamin A is formulated at a high concentration, the composition of the invention is suited as a corneal damage-treating ophthalmic composition showing a better effect and also as a dry eye drug. It is to be noted that dry eyes mean such a state that the cornea and conjunctiva on the surface of the eyeball are damaged owing to the qualitative and quantitative abnormality of the lacrimal fluid. The lacrimal fluid is constituted of three layers including an oil layer, an aqueous layer and a mucin layer, and if the qualitative and quantitative balance of this three-layered structure is disrupted, the lacrimal fluid becomes unstable, thereby leading to a corneal disorder and bringing about dry eyes. In the dry eye treatment, importance is placed on the recovery of the three-layered structure of an oil layer, aqueous layer and mucin layer of the lacrimal fluid and the treatment of the corneal disorder. Since contact lens users are liable to suffer dry eyes, the ophthalmic composition of the invention is suitable as an eye drop for contact lens, an eye wash to be used after removal of contact lenses, a solution to be used upon wearing of contact lenses, and a solution to be used when removing contact lenses. Where used as a dry eye treating agent, a better effect is shown by placing drops of 30 to 60 μL per single use and 3 to 6 cycles per day in the eye.

EXAMPLES

The invention is particularly described by way of Examples and Comparative Examples, and the invention should not be construed as limited to the Examples. It will be noted that amounts in tables are those of pure ingredients.

Examples 1 to 28, Comparative Examples 1 to 5

Ophthalmic compositions (eye drops) having formulations indicated in Tables 1 to 7 were obtained by preliminarily dissolving vitamin A, polyoxyethylene polyoxypropylene glycol and, if necessary, an antioxidant at 85° C., solubilizing the preliminarily dissolved matter in sterilized purified water heated to 85° C., adding water-soluble ingredients such as trometamol, and adjusting the pH (20° C.) to 7.0. 15 mL of the resulting ophthalmic composition was filled in a 15 mL eye-drop container (made of polyethylene terephthalate). The ophthalmic compositions of the examples had satisfactory antiseptic capacity.

<Residual Ratio of Retinol Palmitate (%)>

The content of retinol palmitate in the ophthalmic composition was measured immediately after the preparation and six months after storage at 40° C. and 75% R.H. (severe test). The measurement was made by use of a high-performance liquid chromatographic method. The residual ratio (%) of retinol palmitate was calculated from the resulting content of the retinol palmitate based on the following equation.

Residual Ratio (%) of Retinol Palmitate=content of retinol palmitate after the storage/content of retinol palmitate immediately after the preparation× 100

TABLE 1

|  | Formulation (W/V %) | Example 1 | Comparative Example 1 | Comparative Example 2 | Comparative Example 3 | Comparative Example 4 | Comparative Example 5 |
|---|---|---|---|---|---|---|---|
| (A) | Retinol palmitate | 50,000 units | 50,000 units | 50,000 units | 50,000 units | 50,000 units | 50,000 units |
| (B) | Polyoxyethylene (200) polyoxy propylene (70) glycol | 1 | 1 | 0.1 | — | — | — |
| (C) | Trometamol | 1 | — | 1 | — | — | 1 |
| Others | Polyoxyethylene hardened castor oil 60 | — | — | — | 1 | — | — |
|  | Polysorbate 80 | — | — | — | — | 1 | 1 |
|  | Sodium chloride | 0.9 | 0.9 | 0.9 | 0.9 | 0.9 | 0.9 |
|  | Diluted hydrochloric acid/sodium hydroxide (ph = 7) | Appropriate amount | Appropriate amount | Appropriate amount | Appropriate amount | Appropriate amount | Appropriate amount |
|  | Purified water | Balance | Balance | Balance | Balance | Balance | Balance |
|  | Total | 100 mL | 100 mL | 100 mL | 100 mL | 100 mL | 100 mL |
|  | Residual ratio of retinol palmitate (%) | 66.5 | 59.7 | Not solubilized | 57.2 | 57.0 | 57.2 |
|  | units of (A)/g of (B) | 50,000 | 50,000 | 500,000 | 50,000 | 50,000 | 50,000 |
|  | (B):(C) | 1:1 | — | 1:10 | — | — | — |

TABLE 2

|  | Formulation (W/V %) | Example 2 | Example 3 | Example 4 | Example 5 |
|---|---|---|---|---|---|
| (A) | Retinol palmitate | 50,000 units | 50,000 units | 50,000 units | 50,000 units |
| (B) | Polyoxyethylene (200) polyoxypropylene (70) glycol | 0.4 | 1.5 | 3 | 5 |
| (C) | Trometamol | 1 | 1 | 1 | 1 |
| Others | Sodium chloride | 0.9 | 0.9 | 0.9 | 0.9 |
|  | Diluted hydrochloric acid/sodium hydroxide (pH = 7) | Appropriate amount | Appropriate amount | Appropriate amount | Appropriate amount |
|  | Purified water | Balance | Balance | Balance | Balance |
| Total |  | 100 mL | 100 mL | 100 mL | 100 mL |
| Residual ratio of retinol palmitate (%) |  | 64.3 | 66.4 | 65.5 | 64.1 |
| Units of (A)/g of (B) |  | 125,000 | 33,333 | 16,667 | 10,000 |
| (B):(C) |  | 1:2.5 | 1.5:1 | 3:1 | 5:1 |

TABLE 3

|  | Formulation (W/V %) | Example 6 | Example 7 | Example 8 | Example 9 | Example 10 |
|---|---|---|---|---|---|---|
| (A) | Retinol palmitate | 50,000 units | 50,000 units | 50,000 units | 50,000 units | 50,000 units |
| (B) | Polyoxyethylene (200) polyoxypropylene (70) glycol | 1 | 1 | 1 | 1 | 1 |
| (C) | Trometamol | 0.05 | 0.1 | 0.5 | 3 | 5 |
| Others | Sodium chloride | 0.9 | 0.9 | 0.9 | 0.9 | 0.9 |
|  | Diluted hydrochloric acid/sodium hydroxide (ph = 7) | Appropriate amount | Appropriate amount | Appropriate amount | Appropriate amount | Appropriate amount |
|  | Purified water | Balance | Balance | Balance | Balance | Balance |
|  | Total | 100 mL | 100 mL | 100 mL | 100 mL | 100 mL |
|  | Residual ratio of retinol palmitate (%) | 65.3 | 65.8 | 66.4 | 66.7 | 66.9 |
|  | units of (A)/g of (B) | 50,000 | 50,000 | 50,000 | 50,000 | 50,000 |
|  | (B):(C) | 20:1 | 10:1 | 2:1 | 1:3 | 1:5 |

TABLE 4

| Formulation (W/V %) | | Example 11 | Example 12 | Example 13 |
|---|---|---|---|---|
| (A) | Retinol palmitate | 50,000 units | 50,000 units | 50,000 units |
| (B) | Polyoxyethylene (200) polyoxypropylene (700) glycol | 1 | 1 | 1 |
| (C) | Trometamol | 1 | 1 | 1 |
| (D) | d-α-Tocopherol acetate | — | 0.05 | 0.05 |
| | Dibutylhydroxytoluene | 0.005 | — | 0.005 |
| Others | Polyoxyethylene hardened castor oil 60 | — | — | — |
| | Sodium chloride | 0.9 | 0.9 | 0.9 |
| | Diluted hydrochloric acid/sodium hydroxide (pH = 7) | Appropriate amount | Appropriate amount | Appropriate amount |
| | Purified water | Balance | Balance | Balance |
| | Total | 100 mL | 100 mL | 100 mL |
| | Residual ratio of retinol palmitate (%) | 68.5 | 68.7 | 70.9 |
| | units of (A)/g of (B) | 50,000 | 50,000 | 50,000 |
| | (B):(C) | 1:1 | 1:1 | 1:1 |

TABLE 5

| Formulation (W/V %) | | Example 14 | Example 15 | Example 16 | Example 17 | Example 18 | Example 19 |
|---|---|---|---|---|---|---|---|
| (A) | Retinol palmitate | 50,000 units | 50,000 units | 50,000 units | 100,000 units | 200,000 units | 300,000 units |
| (B) | Polyoxyethylene (200) polyoxypropylene (70) glycol | 1 | 1 | 1 | 3 | 5 | 5 |
| (C) | Trometamol | 0.1 | 0.5 | 2 | 2 | 3 | 5 |
| (D) | d-α-Tocopherol acetate | 0.05 | 0.05 | 0.05 | 0.2 | 0.05 | 0.05 |
| | Dibutylhydroxytoluene | 0.005 | 0.005 | 0.005 | 0.005 | 0.005 | 0.005 |
| Others | Sodium hyaluronate | — | — | 0.02 | — | 0.02 | — |
| | Hypromellose | — | — | 0.1 | — | — | 0.1 |
| | Polyvinylpyrrolidone | — | 0.1 | — | — | — | 0.1 |
| | Sodium chondroitin sulfate | 0.1 | — | — | 0.1 | — | — |
| | Taurine | — | 0.1 | 0.1 | — | — | 0.1 |
| | Potassium L-aspartate | 1 | — | — | 1 | — | — |
| | Boric acid | 0.5 | 0.5 | 0.5 | 0.5 | 0.5 | 0.5 |
| | Borax | — | — | — | 0.2 | — | — |
| | l-Menthol | — | 0.005 | — | — | — | — |
| | dl-Camphor | — | 0.002 | — | — | — | — |
| | d-Borneol | — | 0.003 | — | — | — | — |
| | Sodium edetate | 0.1 | 0.1 | 0.1 | 0.1 | 0.1 | 0.1 |
| | Potassium sorbate | — | — | — | 0.1 | — | — |
| | Glycerine | — | 0.5 | — | — | — | — |
| | Sodium chloride | 0.9 | 0.9 | 0.9 | 0.9 | 0.9 | 0.9 |
| | Dilute hydrochloric acid/sodium hydroxide (pH = 7) | Appropriate amount | | | | | |
| | Purified water | Balance | | | | | |
| | Total | 100 mL | 100 mL | 100 mL | 100 mL | 100 mL | 100 mL |
| | Residual ratio of retinol palmitate (%) | 70.5 | 70.6 | 70.8 | 67.3 | 66.5 | 66.1 |
| | units of (A)/g of (B) | 50,000 | 50,000 | 50,000 | 33,333 | 40,000 | 60,000 |
| | (B):(C) | 10:1 | 2:1 | 1:2 | 1.5:1 | 1.7:1 | 1:1 |

TABLE 6

| Formulation (W/V %) | | Example 20 | Example 21 | Example 22 | Example 23 | Example 24 |
|---|---|---|---|---|---|---|
| (A) | Retinol palmitate | 50,000 units | 50,000 units | 50,000 units | 50,000 units | 100,000 units |
| (B) | Polyoxyethylene (200) polyoxypropylene (70) glycol | 0.4 | 1 | 2 | 5 | 3 |
| (C) | Trometamol | 1 | 1 | 2 | 2 | 0.5 |
| (D) | d-α-Tocopherol acetate | 0.05 | 0.05 | 0.1 | 0.05 | 1 |
| | Dibutylhydroxytoluene | 0.005 | 0.005 | 0.005 | 0.005 | 0.005 |
| Others | Tetrahydrozoline hydrochloride | 0.05 | | 0.05 | | |
| | Neostigmine methysulfate | 0.005 | — | 0.005 | — | — |

TABLE 6-continued

| Formulation (W/V %) | Example | | | | |
|---|---|---|---|---|---|
| | 20 | 21 | 22 | 23 | 24 |
| Chlorpheniramine maleate | 0.03 | 0.03 | 0.03 | 0.03 | 0.03 |
| Pyridoxine hydrochloride | — | 0.05 | 0.05 | 0.05 | 0.05 |
| Dipotassium glycyrrhizate | — | — | — | — | 0.25 |
| Sodium hyaluronate | 0.02 | — | — | — | 0.02 |
| Boric acid | 1 | 1 | 1 | 1 | 1 |
| Borax | 0.5 | 0.5 | 0.5 | 0.5 | 0.5 |
| l-Menthol | 0.005 | — | — | — | 0.005 |
| dl-Camphor | 0.002 | — | — | — | 0.002 |
| d-Borneol | 0.003 | — | — | — | 0.003 |
| Sodium edetate | 0.1 | 0.1 | 0.1 | 0.1 | 0.1 |
| Potassium sorbate | — | — | — | — | 0.1 |
| Glycerine | — | — | — | — | 0.2 |
| Glucose | — | — | — | — | 0.1 |
| Sodium chloride | 0.9 | 0.9 | 0.9 | 0.9 | 0.9 |
| Diluted hydrochloric acid/sodium hydroxide (pH = 7) | | Appropriate amount | | | |
| Purified water | | Balance | | | |
| Total | 100 mL | 100 mL | 100 mL | 100 mL | 100 mL |
| Residual ratio of retinol palmitate (%) | 70.1 | 70.5 | 70.6 | 70.7 | 67.1 |
| units of (A)/g of (B) | 125,000 | 50,000 | 25,000 | 10,000 | 33,333 |
| (B):(C) | 1:2.5 | 1:1 | 1:1 | 2.5:1 | 6:1 |

TABLE 7

| | Formulation (W/V %) | Example | | | |
|---|---|---|---|---|---|
| | | 25 | 26 | 27 | 28 |
| (A) | Retinol palmitate | 200,000 units | 300,000 units | 300,000 units | 500,000 units |
| (B) | Polyoxyethylene (200) polyoxypropylene (70) glycol | 5 | 5 | 2.5 | 2.5 |
| | Polyoxyethylene (160) polyoxypropylene (30) glycol | — | — | 2.5 | — |
| | Polyoxyethylene (54) polyoxypropylene (39) glycol | — | — | — | 2.5 |
| (C) | Trometamol | 2 | 5 | 3 | 3 |
| (D) | d-α-Tocopherol acetate | 0.05 | 0.05 | 0.05 | 0.05 |
| | Dibutylhydroxytoluene | 0.005 | 0.005 | 0.005 | 0.005 |
| Others | Tetrahydrozoline hydrochloride | 0.05 | — | — | 0.05 |
| | Neostigmine methylsulfate | 0.005 | — | — | 0.005 |
| | Chlorpheniramine maleate | 0.03 | 0.03 | 0.03 | 0.03 |
| | Pyridoxine hydrochloride | 0.05 | 0.05 | 0.05 | 0.05 |
| | Dipotassium glycyrrhizate | — | 0.25 | — | — |
| | Sodium hyaluronate | — | — | — | 0.02 |
| | Boric acid | 1 | 1 | 1 | 1 |
| | Borax | 0.5 | 0.5 | 0.5 | 0.5 |
| | l-Menthol | — | 0.005 | — | 0.2 |
| | dl-Camphor | — | 0.002 | — | — |
| | d-Borneol | — | 0.003 | — | — |
| | Sodium edetate | 0.1 | 0.1 | 0.1 | 0.1 |
| | Potassium sorbate | — | — | — | 0.1 |
| | Propylene glycol | — | 0.1 | — | — |
| | Glucose | — | — | 0.1 | — |
| | Sodium chloride | 0.9 | 0.9 | 0.9 | 0.9 |
| | Dilute hydrochloric acid/ sodium hydroxide (pH = 7) | | Appropriate amount | | |
| | Purified water | | Balance | | |
| Total | | 100 mL | 100 mL | 100 mL | 100 mL |
| Residual ratio of retinol palmitate (%) | | 66.8 | 66.2 | 66.4 | 66.1 |
| units of (A)/g of (B) | | 40,000 | 60,000 | 60,000 | 100,000 |
| (B):(C) | | 2.5:1 | 1:1 | 1:1.2 | 1:1.2 |

Comparative Examples 6 and 7

Ophthalmic compositions (eye drops) having formulations indicated in Table 8 were prepared according to Example 1 and were evaluated according to the following methods with respect to the corneal and conjunctival disorder treating effect and also to the eye irritation to provide an index for dry eye treatment. The results are shown in the table along with the results of Example 1.
<Corneal and Conjunctival Disorder Treating Effect>
Test for corneal and conjunctival disorder treating effect using a heptanol-treated rabbit corneal and conjunctival epithelium disorder model Rabbits were subjected to heptanol treatment (by dropping 200 μL per eye of a mixed solution of heptanol/ethanol=8:2) to provide a model suffered from a disorder at the corneal and conjunctival epithelium of the rabbit. Thereafter, the respective samples were continuously applied to the eyes over 11 days (six cycles (100 μL/cycle)/day). During the course of the drops in the eyes, fluorescein staining was carried out periodically (by dropping 50 μL per eye of 2% fluorescein), under which the corneal and conjunctival disorder treating effect was evaluated based on the Lenp judgment standards on a fifteen point-scale (a score immediately after the heptanol treatment was set at 15 points and decreased according to the degree of improvement). The results of the evaluation at the fifth day are shown.
<Eye Irritation>

Rabbits were subjected to a ultrafrequent eye drop test wherein 15 dropping cycles at 50 μL/cycle were carried out at intervals of five minutes.

After the fifteenth dropping cycle, fluorescein staining was carried out (by dropping 50 μL per eye of 2% fluorescein), and the corneal disorder range was evaluated according to the following standards.

Score 4: Staining was found at least ⅔ of the total area of the cornea.

Score 3: Staining was found at from least ⅓ to less than ⅔ of the total area of the cornea.

Score 2: Staining was found at less than ⅓ of the total area of the cornea.

Score 1: Staining was slightly found.

Score 0: No staining was found.

TABLE 8

| | | Example | Comparative Example | |
|---|---|---|---|---|
| | Formulation (W/V%) | 1 | 6 | 7 |
| (A) | Retinol Palmitate | 50,000 units | — | 50,000 units |
| (B) | Polyoxyethylene (200) polyoxypropylene (70) glycol | 1 | 1 | — |
| (C) | Trometamol | 1 | 1 | 1 |
| Others | Polyoxyethylene hardened castor oil 60 | — | — | 1 |
| | Polysorbate 80 | — | — | — |
| | Sodium chloride | 0.9 | 0.9 | 0.9 |
| | Diluted hydrochloric acid/sodium hydroxide (pH = 7) | Appropriate amount | Appropriate amount | Appropriate amount |
| | Purified water | Balance | Balance | Balance |
| Total | | 100 mL | 100 mL | 100 mL |
| Corneal and conjunctival disorder treating effect | | 9 | 13 | 12 |
| Eye irritation | | 0 | 0 | 0 |

Examples 29 to 33

The ophthalmic compositions of Table 9 were prepared according to Example 1 and the residual ratio of retinol palmitate, corneal and conjunctival disorder treating effect and eye irritation were evaluated according to the above-stated methods. The results are also shown in the Table.

TABLE 9

| | | Example | | | | |
|---|---|---|---|---|---|---|
| | Formulation (W/V %) | 29 | 30 | 31 | 32 | 33 |
| (A) | Retinol palmitate | 100,000 units | 150,000 units | 200,000 units | 300,000 units | 500,000 units |
| (B) | Polyoxyethylene (200) polyoxypropylene (70) glycol | 2 | 1 | 5 | 5 | 5 |
| (C) | Trometamol | 1 | 1 | 1 | 5 | 5 |
| (D) | d-α-Tocopherol acetate | 0.05 | 0.05 | 0.05 | 0.05 | 0.05 |
| | Dibutylhydroxytoluene | 0.005 | 0.5 | 0.005 | 0.005 | 0.005 |
| Others | Sodium chloride | 0.9 | 0.9 | 0.9 | 0.9 | 0.9 |
| | Diluted hydrochloric acid/sodium hydroxide (pH = 7) | Appropriate amount | Appropriate amount | Appropriate amount | Appropriate amount | Appropriate amount |
| | Purified water | Balance | Balance | Balance | Balance | Balance |
| | Total | 100 mL | 100 mL | 100 mL | 100 mL | 100 mL |
| | Residual ratio of retinol palmitate (%) | 67.2 | 66.4 | 66.3 | 66.5 | 66.2 |
| | Corneal and conjunctival disorder treating effect | 9 | 8 | 8 | 6 | 6 |
| | Eye irritation | 0 | 0 | 0 | 0 | 0 |
| | Units of (A)/g of (B) | 50,000 | 150,000 | 40,000 | 60,000 | 100,000 |
| | (B):(C) | 2:1 | 1:1 | 5:1 | 1:1 | 1:1 |

The starting materials used in the examples are indicated below.

Polyoxyethylene (200) polyoxypropylene (70) glycol:
Uniloob 70DP-950B, Japanese Pharmaceutical Excipients, NFO Corporation, or Lutrol F127, Japanese Pharmaceutical Excipients, BASF Japan Ltd.

Polyoxyethylene (160) polyoxypropylene (30) glycol:
Pronon#188P, Japanese Pharmaceutical Excipients, NFO Corporation Polyoxyethylene (54) polyoxypropylene (39) glycol:
Pronon#235P, Japanese Pharmaceutical Excipients, NFO Corporation Polyoxyethylene hardened castor oil 60:
HCO-60 (for medical purposes), Japanese Pharmaceutical Excipients, Nikko Chemicals Co., Ltd.

Polysorbate 80:
Rheodol TW-0120V, Japanese Pharmacopoeia, Kao Corporation Hypromellose:
Metolose 65SH-4000, Japanese Pharmacopoeia, Shin-Etsu Chemical Co., Ltd.

Polyvinylpyrrolidone:
Kollidon 90F, Japanese Pharmacopoeia, BASF

The invention claimed is:

1. An ophthalmic composition comprising
(A) 50,000 to 500,000 units/100 mL of vitamin A,
(B) 0.4 to 5 W/V % of polyoxyethylene polyoxypropylene glycol, and
(C) trometamol,
wherein a ratio being expressed as [(A) vitamin A units/100 mL]/[(B) polyoxyethylene polyoxypropylene glycol g/100 mL] is 10,000 to 150,000.

2. The ophthalmic composition as defined in claim 1, wherein a content of the ingredient (A) is at least 100,000 units/100 mL.

3. The ophthalmic composition as defined in claim 1, wherein a content of the ingredient (A) is at least 200,000 units/100 mL.

4. The ophthalmic composition as defined in claim 1, wherein a content of the ingredient (A) is at least 300,000 units/100 mL.

5. The ophthalmic composition as defined in any one of claims 1 to 4, further comprising (D) an antioxidant.

6. The ophthalmic composition as defined in claim 5, wherein the ingredient (D) is vitamin E and/or dibutylhydroxytoluene.

7. The ophthalmic composition as recited in claim 1, wherein the ingredient (A) is retinol palmitate, retinol acetate or retinoic acid.

8. The ophthalmic composition as defined in claim 1, wherein a ratio by weight between the ingredient (B) and the ingredient (C) expressed as (B):(C) is at 1:30 to 30:1.

9. The ophthalmic composition as defined in claim 1, wherein a ratio by weight between the ingredient (B) and the ingredient (C), the weight ratio being expressed as (B):(C), is at 1:5 to 20:1.

10. The ophthalmic composition as recited in claim 1, wherein the polyoxyethylene in the polyoxyethylene polyoxypropylene glycol ingredient (B) has an average degree of polymerization of ethylene oxide of 20 to 200 and wherein the polyoxypropylene in the polyoxyethylene polyoxypropylene glycol ingredient (B) has an average degree of polymerization of propylene oxide of 20 to 70.

11. The ophthalmic composition as defined in claim 1, wherein a content of trometamol ingredient (C) is 0.1 to 3 W/V % relative to the total amount of the ophthalmic composition.

12. The ophthalmic composition as defined in claim 1, further comprising as an antioxidant ingredient (D) d-α-tocopherol.

13. The ophthalmic composition as defined in claim 1, further comprising as an antioxidant ingredient (D) a combination of vitamin E and dibutylhydroxytoluene.

14. The ophthalmic composition as defined in claim 1, which is obtained by solubilizing (A) vitamin A in sterilized purified water with the aid of (B) polyoxyethylene polyoxypropylene glycol, followed by adding (C) trometamol.

* * * * *